United States Patent [19]
Fumihiko

[11] Patent Number: 5,593,587
[45] Date of Patent: Jan. 14, 1997

[54] CELL STRAINER

[75] Inventor: Hato Fumihiko, Sakai, Japan

[73] Assignee: Becton, Dickinson and Company, Franklin Lakes, N.J.

[21] Appl. No.: 175,431

[22] PCT Filed: Jul. 8, 1992

[86] PCT No.: PCT/JP92/00878

§ 371 Date: Jan. 25, 1994

§ 102(e) Date: Jan. 25, 1994

[87] PCT Pub. No.: WO93/01271

PCT Pub. Date: Jan. 21, 1993

[30] Foreign Application Priority Data

Jul. 8, 1991 [JP] Japan .................. 3-052535 U

[51] Int. Cl.$^6$ ............................ B01D 29/085
[52] U.S. Cl. .......... 210/470; 210/474; 210/484; 210/497.2; 422/101
[58] Field of Search ................... 210/474, 476, 210/477, 481, 495, 484, 359, 470, 471, 473, 497.01, 497.2, 497.3, 499; 422/99, 101

[56] References Cited

U.S. PATENT DOCUMENTS 2,839,056  6/1958  Mailly ............................ 210/473
4,131,549  12/1978  Ferrara .......................... 210/359

Primary Examiner—Robert A. Dawson
Assistant Examiner—W. L. Walker
Attorney, Agent, or Firm—Nanette S. Thomas

[57] ABSTRACT

A cell strainer to be equipped at the top of a tube for removing impurities, such as supporting tissues, speculae, etc. from a suspension of cells or tissues comprising:

a) a flange to be held by the upper opening of said tube, b) a grip externally projecting from said flange, c) a section which holds a filter having d) a frame body provided below said flange being housed in the opening of a tube, e) a filter component equipped with a frame body extending below the section holding said filter, which receives and filters said suspension, characterized in that said filter component of said cell strainer is formed of a nylon net having a pore size of 40–200 microns.

2 Claims, 2 Drawing Sheets

CELL STRAINER

BACKGROUND ART

The present invention relates to an improved cell strainer, and more particularly to a cell strainer for removing impurities such as supporting tissues and spiculae from a suspension when such a suspension containing lymphocytes is to be prepared for immunological study purposes and lymphocyte to be used for cell fusion are collected in a test tube.

Gauze was conventionally used for collecting the cells noted above. However, the recovery rate of a filtrate lowered as a liquid to be filtered was absorbed by gauze, which readily absorbs water.

DISCLOSURE OF INVENTION

After extensive studies of filter materials other than gauze, the inventor of the present invention has developed a cell strainer made of nylon net having a pore size of 40–200 mm whose filter mesh is capable of removing impurities such as supporting tissues and spiculae from a suspension containing lymphocytes as a large volume of filtrate to be processed is not absorbed by a filter mesh, as the filter mesh itself does not absorb water.

The present invention is a cell strainer to be equipped at the top of a tube for removing impurities from a suspension of cells or tissues comprising:

a) a flange held by the upper opening of said tube, b) a grip externally projecting from said flange, c) a section which holds a filter having d) a frame body provided below said flange being housed in the opening of a tube, e) a filter component equipped with a frame body extending below the section holding said filter, which receives and filters the above-mentioned suspension, characterized in that said filter component of said cell strainer is formed of a nylon net having a pore size of 40–200 mm.

The structure of the body frame is not critical in the present invention.

BEST MODE FOR CARRYING OUT THE INVENTION

Figure 1:
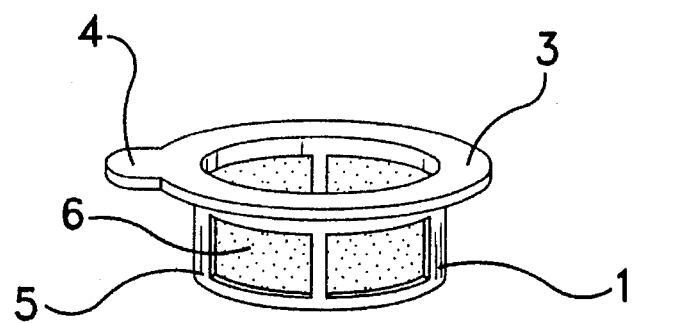
FIG. 1 is a perspective view of a cell strainer and tube embodying the present invention.
Figure 1:
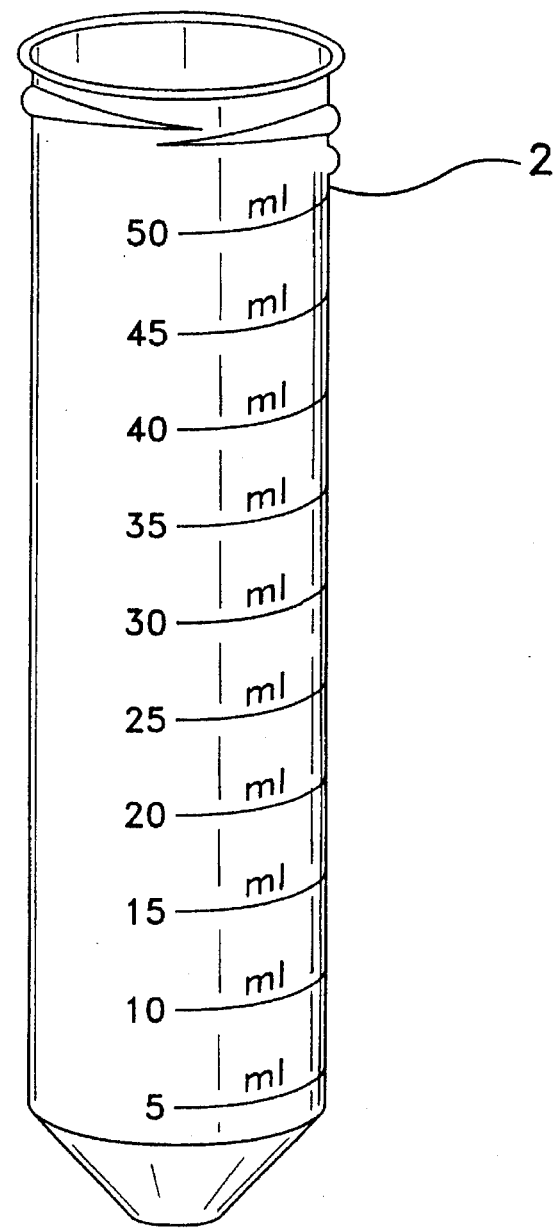

FIG. 1 is a perspective view of a cell strainer and tube of the present invention whose embodiments are further illustrated in detail by the accompanying drawing in which:

cell strainer 1 has a flange 3 being held by the upper opening of a tube 2, a grip 4 externally projecting from said flange, a frame body 5 extending downward and housed in a tube below said flange, and a section holding said filter has a filter component 6 composed of nylon net having pore sizes range from 40 to 200 microns.

It is desirable for the lower end of a frame body extended below a section that holds a filter to have an outer diameter substantially corresponding to an inner diameter of a tube.

The uses of a cell strainer of the present invention are as follows.

1. Supporting tissues and cell packets can be removed when a single cell suspension is prepared from various organs.
2. Products of cytolysis and cell packets can be removed when isolated cell groups are obtained from cultured cells.
3. This cell strainer can be used for filtration of various liquid samples.
4. This cell strainer can be used not only for the removal but also for the collection of various residues on a strainer.

INDUSTRIAL APPLICABILITY

Cell suspension (sample) can be prepared from various organs and cultured cells using different methods, when a sample liquid is poured over a cell strainer placed on a tube such as Falcon (Trademark) 2070 (Blue Max), using KOMAGOME (Tradename) pippet. This makes it possible to obtain a higher recovery ratio and a single cell suspension.

Sample Application

1. Preparation of single cell suspension of blood cells from bone marrow, spleen, thymus, tonsil, lymph node, etc.
2. Preparation of cultured tissue cell samples.
3. Preparation of cultured cell samples for cryopreservation.
4. Preparation of immunogenic cell samples.
5. Removal of agglutinated proteins to be developed in inactivated serum.

EXAMPLE

As for the volumes given in Table 1. The volumes of normal saline solution absorbed by a cell strainer of this invention and gauze were studied.

TABLE 1

| Liquid volume (ml) | Cell strainer (200 mesh) | | | 2 Sheets of 2 × 30 mesh gauze (50 mesh) | | |
|---|---|---|---|---|---|---|
| | Recovered liquid volume (ml) | Mean (ml) | Recovery ratio (%) | Recovered liquid volume (ml) | Mean (ml) | Recovery ratio (%) |
| 50 | 49.98 | 49.87 ± | 99.7 ± | 48.00 | 47.01 ± | 94.02 ± |
| | 49.68 | 0.11 | 0.23 | 46.84 | 0.58 | 0.16 |
| | 49.90 | | | 46.61 | | |
| | 49.92 | | | 47.00 | | |
| | 49.89 | | | 46.58 | | |
| 40 | 39.90 | 39.93 ± | 99.8 ± | 36.82 | 37.11 ± | 92.78 ± |
| | 39.85 | 0.05 | 0.13 | 36.85 | 0.40 | 0.99 |
| | 39.97 | | | 37.23 | | |
| | 39.96 | | | 36.90 | | |
| | 39.95 | | | 37.76 | | |
| 30 | 29.95 | 29.93 ± | 99.8 ± | 27.50 | 27.70 ± | 92.33 ± |
| | 29.99 | 0.06 | 0.19 | 27.89 | 0.40 | 1.33 |
| | 29.84 | | | 27.50 | | |
| | 29.92 | | | 27.30 | | |
| | 29.88 | | | 28.30 | | |
| 20 | 19.98 | 19.89 ± | 99.5 ± | 18.08 | 17.79 ± | 88.95 ± |
| | 19.98 | 0.13 | 0.74 | 18.40 | 0.89 | 4.47 |
| | 19.97 | | | 18.75 | | |
| | 19.67 | | | 17.00 | | |
| | 19.87 | | | 16.70 | | |
| 10 | 9.95 | 9.91 ± | 99.1 ± | 8.93 | 8.54 ± | 85.4 ± |
| | 9.90 | 0.07 | 0.66 | 9.30 | 0.73 | 7.35 |
| | 9.91 | | | 9.08 | | |

TABLE 1-continued

| | Cell strainer (200 mesh) | | | 2 Sheets of 2 × 30 mesh gauze (50 mesh) | | |
|---|---|---|---|---|---|---|
| Liquid volume (ml) | Recovered liquid volume (ml) | Mean (ml) | Recovery ratio (%) | Recovered liquid volume (ml) | Mean (ml) | Recovery ratio (%) |
| | 9.80 | | | 8.20 | | |
| | 9.97 | | | 8.95 | | |
| | | | | 7.22 | | |
| | | | | 8.10 | | |
| 5 | 4.81 | 4.92 ± 0.07 | 98.4 ± 0.14 | 4.21 | 4.13 ± 0.12 | 82.68 ± 2.45 |
| | 4.97 | | | 4.06 | | |
| | 4.93 | | | 3.99 | | |
| | 4.99 | | | 4.30 | | |
| | 4.91 | | | 4.11 | | |
| 4 | 3.92 | 3.94 ± 0.03 | 98.4 ± 0.76 | 2.90 | 3.15 ± 0.19 | 78.75 ± 4.77 |
| | 3.93 | | | 3.20 | | |
| | 3.95 | | | 3.15 | | |
| | 3.98 | | | 3.42 | | |
| | 3.90 | | | 3.06 | | |
| 3 | 2.92 | 2.93 ± 0.03 | 97.7 ± 0.89 | 2.32 | 2.23 ± 0.09 | 74.33 ± 2.97 |
| | 2.91 | | | 2.27 | | |
| | 2.91 | | | 2.27 | | |
| | 2.97 | | | 2.17 | | |
| | 2.95 | | | 2.10 | | |
| 2 | 1.82 | 1.93 ± 0.06 | 96.6 ± 3.21 | 1.40 | 1.32 ± 0.08 | 66.20 ± 3.51 |
| | 1.98 | | | 1.21 | | |
| | 1.94 | | | 1.28 | | |
| | 1.96 | | | 1.33 | | |
| | 1.96 | | | 1.38 | | |
| 1 | 0.91 | 0.95 ± 0.03 | 95.2 ± 3.03 | 0.71 | 0.60 ± 0.07 | 60.00 ± 6.68 |
| | 0.95 | | | 0.54 | | |
| | 0.97 | | | 0.57 | | |
| | 0.99 | | | 0.59 | | |
| | 0.94 | | | 0.53 | | |
| | | | | 0.63 | | |

Although there was the difference between a cell strainer and gauze in the recovery ratios which were 99.7% by the former and 94.02% by the latter, the difference became notable when the volume became as small as 40, 30 and 20 ml, respectively. In particular, when a cell strainer and gauze were compared in their absorption of 1 ml liquid, the former proved more advantageous with a ratio of 95.2% against 60.0% of the latter, since more liquid was absorbed by the gauze.

Figure 2:
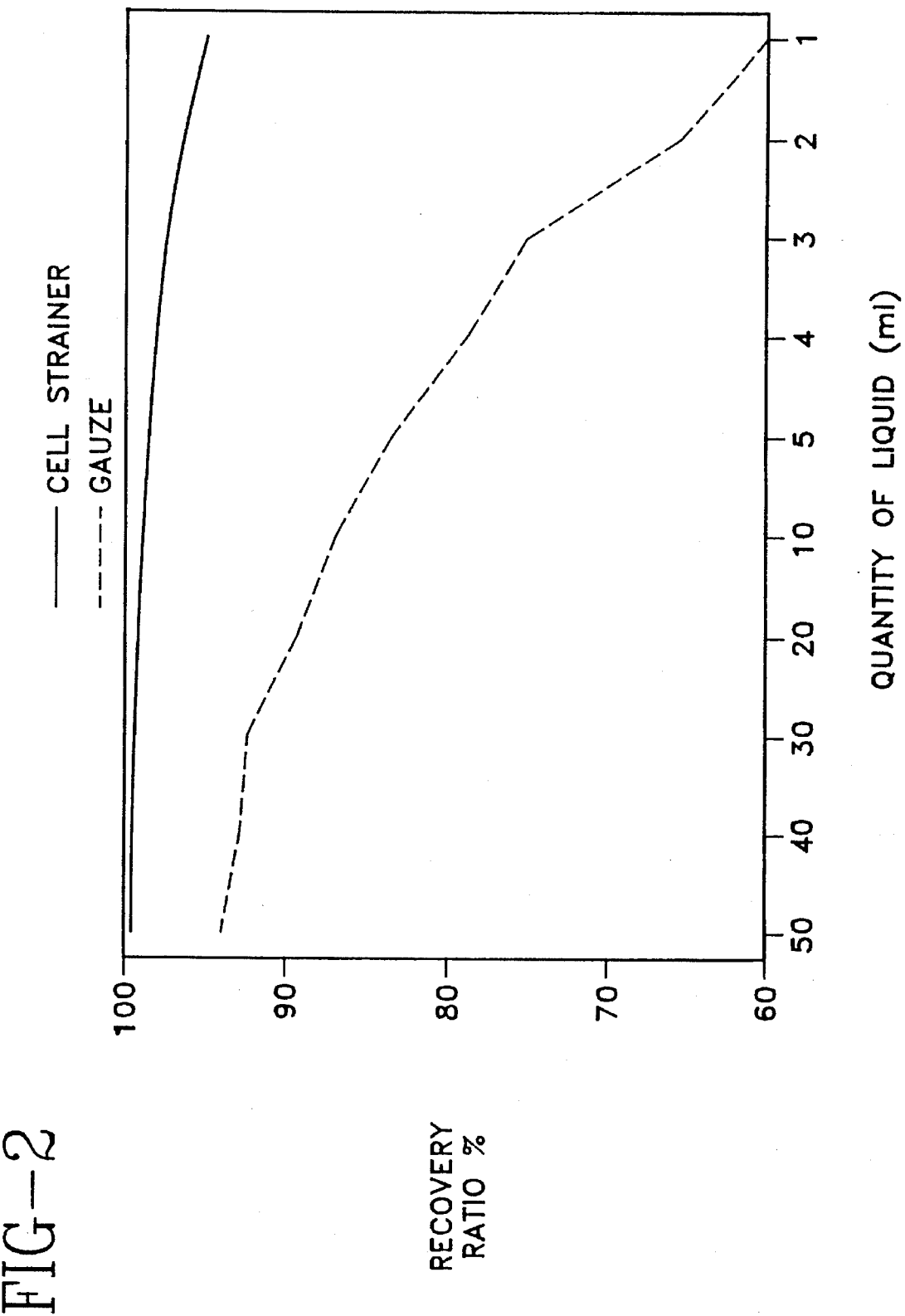
FIG. 2 is a graph showing the difference between a cell strainer and gauze in their absorption of normal saline solution.

The values given in Table 1 are plotted in FIG. 2.

The values given in Table 2 are the significance test results.

Since P<0.001 is the figure that means statistically significant difference, a cell strainer is apparently more acceptable because of its liquid recovery ranging from 1 to 50 ml.

TABLE 2

| | Significance test | | |
|---|---|---|---|
| liquid volume | cell strainer | | gauze |
| 50 ml | 49.87 ± 0.11 | P < 0.001 | 47.00 ± 0.58 |
| 40 ml | 39.93 ± 0.05 | P < 0.001 | 37.11 ± 0.40 |
| 30 ml | 29.93 ± 0.06 | P < 0.001 | 27.70 ± 0.40 |
| 20 ml | 19.89 ± 0.13 | P < 0.001 | 17.79 ± 0.89 |
| 10 ml | 9.91 ± 0.07 | P < 0.001 | 8.54 ± 0.73 |
| 5 ml | 4.92 ± 0.07 | P < 0.001 | 4.13 ± 0.12 |
| 4 ml | 3.94 ± 0.03 | P < 0.001 | 3.15 ± 0.19 |
| 3 ml | 2.93 ± 0.03 | P < 0.001 | 2.23 ± 0.09 |
| 2 ml | 1.93 ± 0.06 | P < 0.001 | 1.32 ± 0.08 |
| 1 ml | 0.95 ± 0.03 | P < 0.001 | 0.60 ± 0.07 |

Table 3 shows the results of test on the adsorption of cells using thymic lymphocytes whose 3 different concentrations were compared. However, it was found that not many cells were adsorptive to a cell strainer or gauze, as the mean adsorption by the former was 98.5%±2.2 that indicates the adsorption of not quite 100%, while the mean adsorption by the latter was 94.0%±4.3.

TABLE 3

| | Cell adsorption (thymic lymphocyte) | |
|---|---|---|
| cell concentration | cell strainer | 2 sheets of gauze (50 mesh) |
| $1 \times 10^8$ cell/ml | 98.2% | 87.8% |
| | 93.5% | 92.6% |
| | 100.0% | 90.1% |
| | 100.0% | 99.2% |
| | mean | mean |
| | 97.9% ± 3.1 | 92.5% ± 4.9 |
| $1 \times 10^7$ cell/ml | 97.0% | 97.8% |
| | 100.0% | 92.8% |
| | 100.0% | 88.5% |
| | 100.0% | 90.2% |
| | mean | mean |
| | 99.4% ± 1.3 | 92.3% ± 4.1 |
| $1 \times 10^6$ cell/ml | 100.0% | 100.0% |
| | 95.8% | 94.4% |
| | 97.1% | 95.7% |
| | 100.0% | 98.8% |
| | mean | mean |
| | 98.2% ± 2.1 | 97.2% ± 2.6 |
| total mean | 98.5% ± 2.2 | 94.0% ± 4.3 |

The cell strainer of the present invention has the following features.

1. Nylon filter in a size of 40–200 mm used for the bottom of a cell strainer does not become wrinkled.
2. This cell strainer can be used at room temperature.
3. This cell strainer can easily be placed on an upper part of a 50 ml centrifuge tube and removed easily as well.
4. handling by a grip prevented contamination of a filter.
5. This cell strainer is sterilized with gamma rays.
6. A peeling-off method is used to open sterilized individual package.

I claim:

1. A cell strainer and tube assembly for removing impurities from a suspension of cells or tissues comprising:

a tube comprising an open end, a closed end, a side wall extending from said open end to said closed end;

a cell strainer associated with said open end of said tube comprising a body frame defining a chamber including an upper portion and a lower portion, said body frame including open sections between said upper portions and said lower portion, a filter component located in said chamber and exposed at said open sections of said body frame; a projecting flange extending radially outwardly from said upper portion; and a grip extending radially outwardly from said flange.

2. The cell strainer and tube assembly of claim 1 wherein said filter component is a nylon net having a pore size of about 40 to about 200 microns.

* * * * *